(12) United States Patent
Kuwabara

(10) Patent No.: US 6,614,524 B1
(45) Date of Patent: Sep. 2, 2003

(54) METHOD OF AND APPARATUS FOR QUALITATIVE ANALYSIS

(75) Inventor: Shoji Kuwabara, Ibaraki (JP)

(73) Assignee: Shimadzu Corporation, Kyoto (JP)

( * ) Notice: Subject to any disclaimer, the term of this patent is extended or adjusted under 35 U.S.C. 154(b) by 854 days.

(21) Appl. No.: 08/854,620

(22) Filed: May 12, 1997

(30) Foreign Application Priority Data

Sep. 30, 1996 (JP) .............................................. 8-259225

(51) Int. Cl.[7] .............................. G01J 3/30; G01J 5/02
(52) U.S. Cl. .............. 356/317; 250/339.09; 250/339.12
(58) Field of Search ...................... 250/339.09, 339.12; 378/45, 48; 356/317

(56) References Cited

U.S. PATENT DOCUMENTS

| | | | | |
|---|---|---|---|---|
| 3,567,928 A | * | 3/1971 | Davies ........................ 250/49.5 |
| 4,260,885 A | * | 4/1981 | Albert ......................... 250/277 |
| 4,362,935 A | * | 12/1982 | Clark, III .................... 378/48 |
| 4,429,409 A | * | 1/1984 | Berry et al. ................. 378/45 |
| 4,719,582 A | * | 1/1988 | Ishida et al. ................ 364/498 |
| 5,218,529 A | * | 6/1993 | Meyer et al. ........... 364/413.01 |
| 5,408,512 A | * | 4/1995 | Kuwabara et al. ............. 378/45 |
| 5,418,826 A | * | 5/1995 | Sato et al. ...................... 378/45 |
| 5,448,070 A | * | 9/1995 | Day et al. ............... 250/339.13 |
| 5,453,613 A | * | 9/1995 | Gray et al. .................. 250/281 |
| 5,528,648 A | * | 6/1996 | Komatsu et al. ............... 378/45 |
| 5,663,997 A | * | 9/1997 | Willis et al. ................... 378/45 |
| 5,668,373 A | * | 9/1997 | Robbat, Jr. et al. ..... 250/339.12 |

\* cited by examiner

Primary Examiner—Zandra V Smith
(74) Attorney, Agent, or Firm—Beyer Weaver & Thomas LLP

(57) ABSTRACT

A qualitative analysis is carried out by first storing reference spectral line data of various elements in different compound forms, exciting a sample and spectroscopically analyzing signal light emitted from the sample to obtain measured spectral line data, determining whether these measured spectral line data include spectral lines of specified compound-forming elements, and comparing the reference spectral line data with the measured spectral line data, if the measured spectral line data are found to include spectral lines of any of the compound-forming elements, to thereby identify elements in the sample.

4 Claims, 2 Drawing Sheets

METHOD OF AND APPARATUS FOR QUALITATIVE ANALYSIS

BACKGROUND OF THE INVENTION

This invention relates to a method of and apparatus for qualitative analysis such as fluorescent X-ray spectrometry and emission spectral analysis wherein a sample is excited and the signal light emitted therefrom is spectroscopically analyzed to identify the elements contained in the sample. More particularly, this invention relates to the technology of carrying out accurate qualitative analyses by eliminating the effects of chemical shifts.

For carrying out a qualitative analysis of a sample with a fluorescent X-ray spectrometer, for example, it has been known to preliminarily store the wavelengths of various elements in a memory device as a database, to find the wavelength corresponding to the detection angle $2\theta$ of each of the peaks of the spectrum obtained from the fluorescent X-ray from the sample, to compare them with the database, and to identify the elements which show values close to those in the database. The target elements to be analyzed in a sample (such as Al, Si, O, S, Mg and B), however, do not always exist in the elemental form but may frequently be in the form of a compound such as an oxide or a nitride. When an element is in the form of a compound, what is known as "the chemical shift" is observed, that is, the peak for that element appears at a shifted wavelength compared to when the element is in the elemental form. FIG. 3 shows how the profile of elemental boron shown by the solid line changes to the one shown by the broken line in the case of $B_2O_3$ where boron appears in a compound with oxygen, the peak shifting by $\Delta 2\theta$.

The chemical shift is generally more pronounced for elements with small atomic numbers, or light elements. It is probably because a light element has only a small number of electrons and its energy state is more likely to be influenced by the conditions of its K-shell electrons due to its chemical bonding. In a situation where the chemical shift $\Delta 2\theta$ is greater than the error in the optical system for measuring the fluorescent X-ray, the measured peak position will not agree with the peak position in the database, and hence the element may fail to be identified, or an element corresponding to an incorrect spectral line may be identified.

SUMMARY OF THE INVENTION

It is therefore an object of this invention to eliminate such problems of incorrectly identifying elements in a qualitative analysis of a sample due to the chemical shift of the elements such that qualitative analyses can be carried out with improved reliability.

An apparatus for qualitative analysis embodying this invention, with which the above and other objects can be accomplished, may be characterized as comprising a data memory for storing measured spectral line data obtained by exciting a sample and spectroscopically analyzing signal light emitted from the sample, a database memory which stores reference spectral line data of various elements in different compound forms, and a data analyzer for determining whether the measured spectral line data include spectral lines of specified compound-forming elements such as oxygen and nitrogen and, if the measured spectral line data include spectral lines of any of these compound-forming elements, comparing the reference spectral line data with the measured spectral line data to thereby identify elements in the sample.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings.

DETAILED DESCRIPTION OF THE INVENTION

Figure 1:
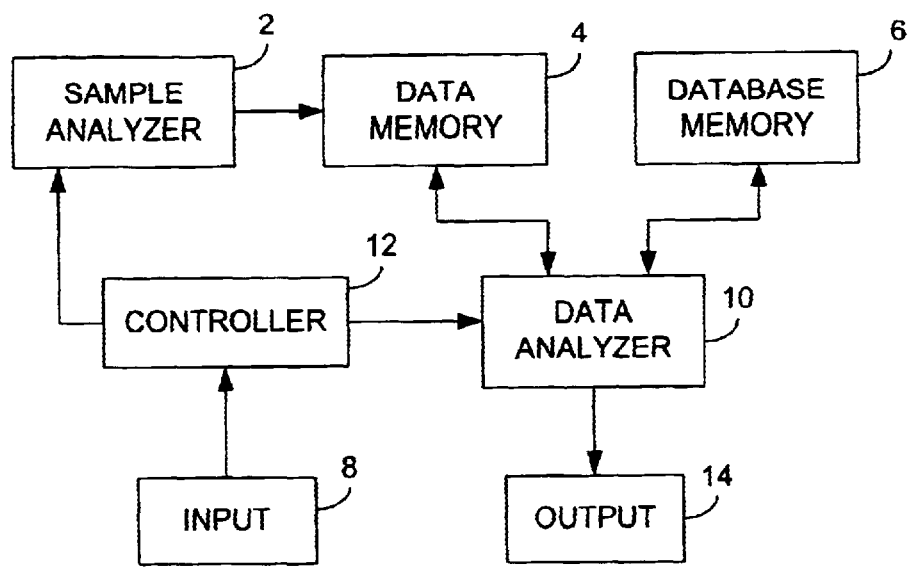
FIG. 1 is a block diagram of an apparatus embodying this invention for analyzing fluorescent X-ray.
Figure 3:
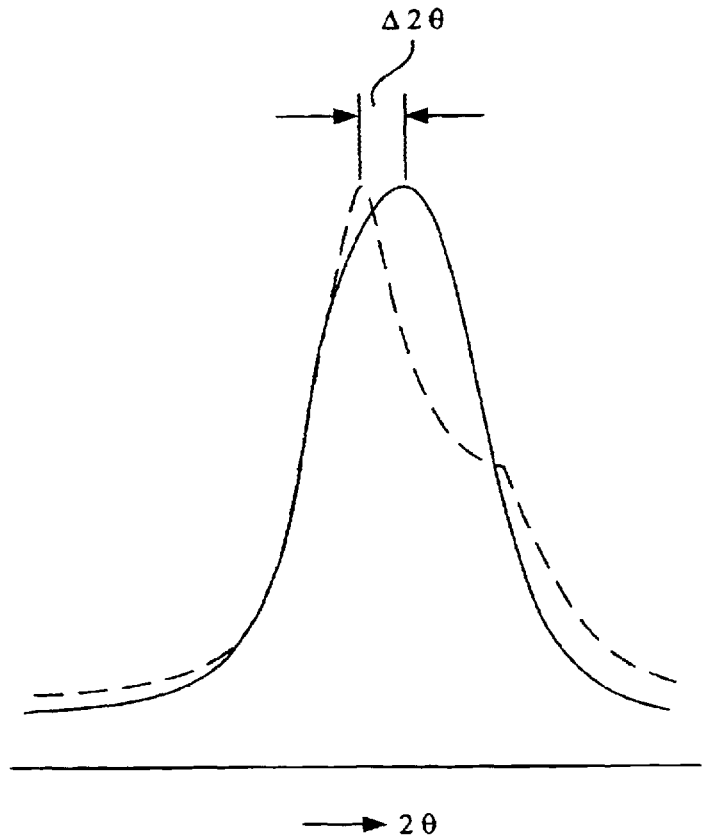
FIG. 3 is a graph illustrating a chemical shift.

The invention is described next by way of an apparatus for analyzing fluorescent X-ray as an example of apparatus for qualitative analysis. As shown in FIG. 1 as a block diagram, this apparatus 1 comprises a sample analyzer 2, a data memory 4, a database memory 6, an input device 8, a data analyzer 10, a controller unit 12 and an output device 14. The sample analyzer 2 includes an X-ray generator, a spectroscope and an X-ray detector (not shown) and serves to spectroscopically analyze the signal light obtained by exciting a sample and to thereby measure the spectral lines of various elements contained in the sample. The data memory 4 may comprise a memory device of a known kind such as a random access memory (RAM) and serves to store the data related to the spectral lines of the sample measured by the sample analyzer 2. The database memory 6 may comprise an external memory. device such as a CD-ROM, and wavelength data of spectral lines of elements in various chemical states such as those of elements as oxides, nitrides, carbides, etc. are preliminarily stored in the database memory 6. For boron, for example, not only the wavelength data of spectral line for elemental boron, but those of compounds of boron with oxygen, nitrogen, carbon, etc. such as $B_2O_3$ and $B_2N_3$, are also stored. In other words, data on every element with the presence of chemical shifts are also stored. In what follows, elements such as oxygen and nitrogen that oxidize another element will be referred to as "oxidizing elements," and elements such as Al, Si, P, S, Mg and B that form a chemical bond with such oxidizing elements will be referred to as "oxidized elements" for convenience.

The input device 8 may comprise an input interface such as a keyboard or a mouse and serves to allow the user to set conditions of measurements by the sample analyzer 2 and of data analysis.

The data analyzer 10 is for determining whether the measured data stored in the data memory 4 contain any spectral line of an oxidizing element such as oxygen and nitrogen necessary for identifying the form of compound. If such an oxidizing element is found to be contained, the database in the database memory 6 is searched for the oxidized elements combined with that oxidizing element and having a chemical shift, and compared with measured data such that the elements contained in the sample can be identified.

The controller unit 12 is for controlling the operations of the sample analyzer 2 and the data analyzer 10 on the basis of data inputted through the input device 8. The data analyzer 10 and the controller unit 12 may comprise a central processing unit (CPU). The output device 14 is for outputting the results of qualitative analysis obtained by the data analyzer 10 and may include display devices such as a CRT and an LCD as well as a printing device such as a printer.

Figure 2:
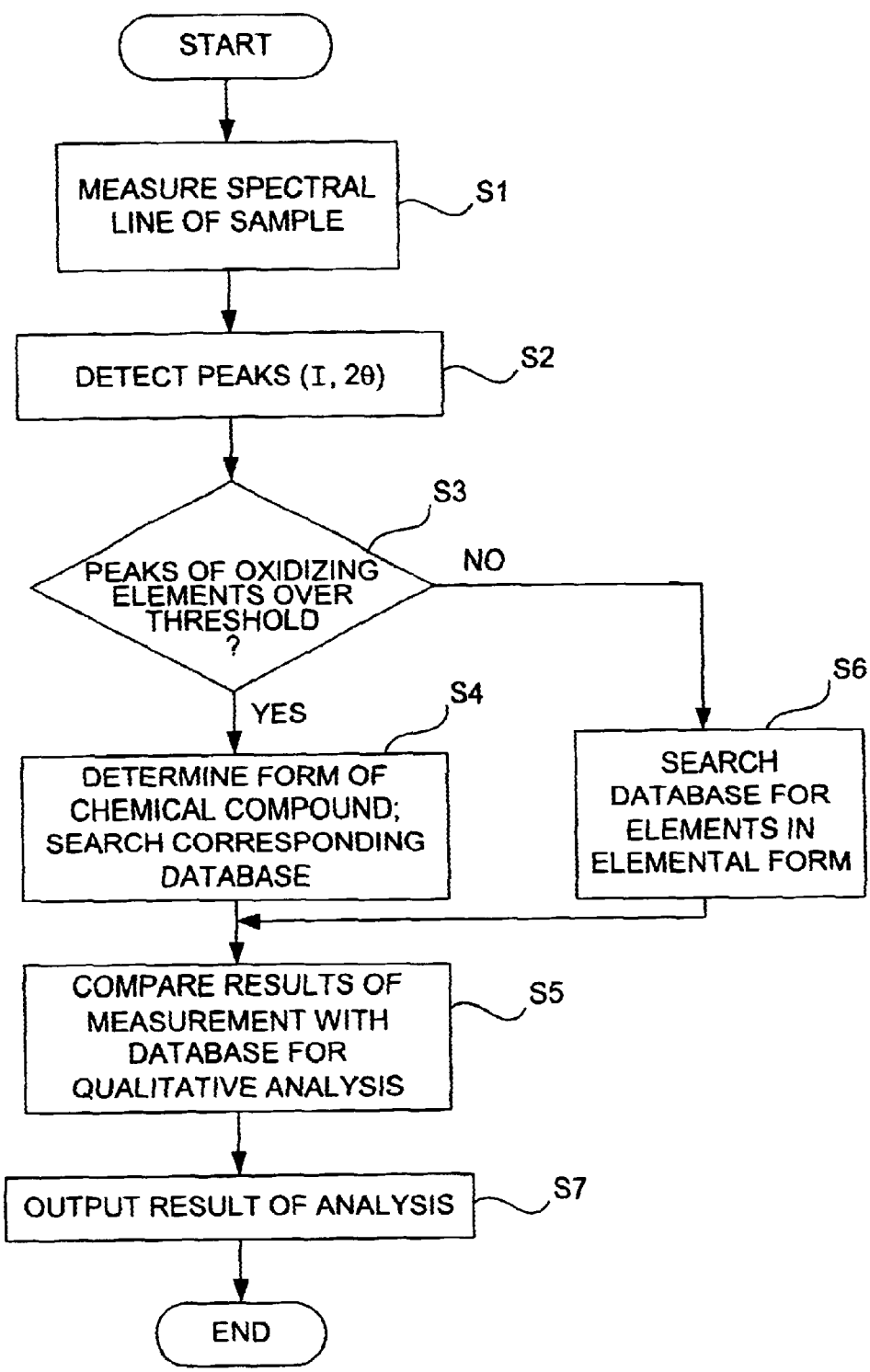
FIG. 2 is a flow chart of a method of qualitative analysis embodying this invention by using an apparatus shown in FIG. 1.

Next, the flow chart of FIG. 2 will be referenced to explain how the qualitative analysis of a sample by the apparatus 1 can be automated.

A qualitative analysis is carried out by exposing a sample to a primary X-ray beam, and the spectral lines of elements contained in the sample are individually measured by means of a spectroscope and a detector for detecting the fluorescent X-rays from the sample (Step S1). Spectral line data of oxidizing elements such as oxygen and nitrogen which form chemical compounds with other elements are also obtained. These measured data of elements obtained by the sample analyzer 2 are stored in the data memory 4. The data thus stored in the data memory 4 are analyzed by the data analyzer 10, and the detection angle θ and intensity I of each peak of these spectral lines are obtained (Step S2). Next, the data analyzer 10 determines whether the data stored in the data memory 4 contain spectral lines of oxidizing elements such as oxygen and nitrogen needed to identify the form of chemical compound (Step S3). This is done by preliminarily setting, as threshold values, the peak intensities corresponding to the contents of oxidizing elements which may be found in the sample as oxide, nitride and carbide, and determining whether the measured intensity of a spectral line of an oxidizing element is greater than the threshold value. Since the effect of chemical shift is relatively small for these oxidizing elements compared to that for oxidized elements, misidentification is conveniently not likely to occur.

If it is determined that such oxidizing elements are present, the data analyzer 10 searches the database memory 6 for the spectral line data of the oxidized elements with which these oxidizing elements are combined to cause chemical shifts (Step S4). If the data analyzer 10 has detected oxygen, as an example of oxidizing element, it is the spectral line data of oxidized elements combined with oxygen that are searched. The data analyzer 10 then compares and matches this database with the measured data to identify the elements contained in the sample (Step S5). In summary, identification of elements is made with the effects of chemical shifts taken into consideration with respect to each element. Thus, displacements in the detection angle due to chemical shifts do not adversely affect the ability of the apparatus to correctly identify spectral lines of elements which are actually present or cause misidentification of elements.

If it is determined in Step S3 that no spectral line of oxidizing element necessary for identifying the form of chemical compound is contained in the measured data, the data analyzer 10 searches the database 6 for the spectral line data of elements in the elemental form (that is, not in a chemically combined form with an oxidizing element) (Step S6). It then compares and matches the measured data with the data in the database to identify the elements contained in the sample (Step S5).

The result of identification by the data analyzer 10 is transmitted to the output device 14 to be displayed on a CRT or an LCD or printed out by a printer (Step S7).

Although the invention was described above by way of a fluorescent X-ray spectrometer, this is not intended to limit the scope of the invention. It goes without saying that the invention can be applied equally effectively to emission spectral analysis or the like. To summarize, one of the merits of this invention is to eliminate the possibility of misidentification in qualitative analyses caused by chemical shifts of spectral lines of elements. Another merit of this invention is realized when a qualitative analysis is carried out automatically. Although a certain allowance must be given around the center of a detection angle in spectral line analyses because of errors in the optical system that is used, the allowance to be given can be significantly reduced according to this invention because the effects of chemical shift need not be taken into consideration. This has the favorable effect of reducing the number of candidate spectral lines to be searched in the analysis and hence the time required for the analysis can also be reduced.

What is claimed is:

1. An apparatus for qualitative analysis for identifying elements contained in a sample by exciting said sample and spectroscopically analyzing signal light emitted from said sample, said apparatus comprising:

a data memory for storing measured spectral line data including chemical shifts obtained from a sample;

a data base memory storing reference spectral line data of various elements in different compound forms; and a data analyzer for determining whether said measured spectral line data include spectral lines of specified compound-forming elements including oxygen, nitrogen and carbon and, if said measured spectral line data include spectral lines of any of said compound-forming elements, comparing said reference spectral line data including chemical shifts with said measured spectral line data to thereby identify elements in said sample.

2. The apparatus of claim 1 wherein said specified compound-forming elements are capable of forming compounds in said different compound forms.

3. A method of qualitative analysis comprising the steps of:

storing reference spectral line data including chemical shifts of various elements in different compound forms;

exciting a sample and spectroscopically analyzing signal light emitted from said sample to obtain measured spectral line data;

storing said measured spectral line data;

determining whether said measured spectral line data include spectral lines of specified compound-forming elements including oxygen, nitrogen and carbon; and comparing said reference spectral line data including chemical shifts with said measured spectral line data, if said measured spectral line data include spectral lines of any of said compound-forming elements, to thereby identify elements in said sample.

4. The method of claim 3 wherein said specified compound-forming elements are capable of forming compounds in said different compound forms.

* * * * *